United States Patent
Wallstein et al.

(10) Patent No.: US 8,454,611 B2
(45) Date of Patent: Jun. 4, 2013

(54) MODULAR PROSTHESIS RASP

(75) Inventors: Stefan Wallstein, Emmingen-Liptingen (DE); Joerg Fritzsche, Frittlingen (DE)

(73) Assignee: Aesculap AG, Tuttlingen (DE)

( * ) Notice: Subject to any disclaimer, the term of this patent is extended or adjusted under 35 U.S.C. 154(b) by 191 days.

(21) Appl. No.: 12/974,496

(22) Filed: Dec. 21, 2010

(65) Prior Publication Data

US 2011/0160733 A1 Jun. 30, 2011

(30) Foreign Application Priority Data

Dec. 23, 2009 (DE) .......................... 10 2009 059 314
Feb. 15, 2010 (DE) .......................... 10 2010 000 419

(51) Int. Cl.
*A61B 17/00* (2006.01)
(52) U.S. Cl.
USPC ................................. 606/85; 606/79; 606/82
(58) Field of Classification Search
USPC .......................................... 606/79–85, 86 R
See application file for complete search history.

(56) References Cited

U.S. PATENT DOCUMENTS

| 5,993,455 A | * | 11/1999 | Noble | ............................. 606/85 |
| 2007/0225821 A1 | | 9/2007 | Reubelt et al. | |

FOREIGN PATENT DOCUMENTS

| DE | 10 2008 020 192 | | 10/2009 |
| DE | 10 2008 020 199 | | 10/2009 |
| DE | 102008020192 A1 | * | 10/2009 |
| WO | 90/03764 | | 4/1990 |

* cited by examiner

*Primary Examiner* — Kevin T Truong
*Assistant Examiner* — Si Ming Lee
(74) *Attorney, Agent, or Firm* — Lipsitz & McAllister, LLC (57) ABSTRACT

A modular prosthesis rasp is provided, having a rasp body with a rasp main body and at least one modular rasp body part connectable to the main body. The rasp main body has a receptacle for receiving the at least one rasp body part. An outer contour is defined by the rasp main body and the at least one rasp body part. The rasp body part receptacle extends from an indentation, defining a distal end of the receptacle, on a lateral side of the rasp main body to a proximal end thereof. A first tangential plane of the lateral side of the outer contour in the region of the indentation and a second tangential plane at a rasp body part contact surface, in the region of the distal end of the receptacle include an indentation angle of less than 85°.

25 Claims, 9 Drawing Sheets

MODULAR PROSTHESIS RASP

CROSS-REFERENCE TO RELATED APPLICATIONS

This application claims the benefit of German patent application number 10 2009 059 314.1 filed on Dec. 23, 2009 and application number 10 2010 000 419.7 filed on Feb. 15, 2010, which are incorporated herein by reference in their entirety and for all purposes.

FIELD OF THE INVENTION

The present invention relates to prosthesis rasps in general, and, quite specifically, to a modular prosthesis rasp with a rasp body comprising a rasp main body and at least one modular rasp body part connectable to the rasp main body, the rasp main body comprising a rasp body part receptacle for receiving the at least one rasp body part in a connected position in which the rasp main body and the at least one rasp body part are connected to each other, and in which the rasp body defines an outer contour defined partly by the rasp main body and partly by the at least one rasp body part, the rasp body part receptacle extending from an indentation, defining a distal end of the rasp body part receptacle, on a lateral side of the rasp main body to a proximal end of the rasp main body.

BACKGROUND OF THE INVENTION

Such a modular prosthesis rasp is known, for example, from DE 10 2008 020 192 A1. It serves, in particular, the purpose of preparing a bone cavity in a patient's femur prior to insertion of a prosthesis stem of a hip joint endoprosthesis and with the modular rasp body part a slot-shaped recess for receiving a fin-like projection on the prosthesis stem.

With the known modular prosthesis rasp it is, however, disadvantageous that while inserting the rasp main body into the medullary cavity of the femur after a partial resection of the trochanter, the trochanter is partly damaged in an undesirable way because the rasp main body comes into contact owing to its outer contour with the trochanter on the lateral side and can injure the trochanter and surrounding soft tissue.

Availability of a modular prosthesis rasp, with which traumatization of the patient is minimized while the rasp main body is being inserted into a bone cavity is, therefore, desirable.

SUMMARY OF THE INVENTION

In a first aspect of the invention, a modular prosthesis rasp comprises a rasp body having a rasp main body and at least one modular rasp body part connectable to the rasp main body. The rasp main body comprises a rasp body part receptacle for receiving the at least one rasp body part in a connected position in which the rasp main body and the at least one rasp body part are connected to each other, and in which the rasp body defines an outer contour defined partly by the rasp main body and partly by the at least one rasp body part. The rasp body part receptacle extends from an indentation, defining a distal end of the rasp body part receptacle, on a lateral side of the rasp main body to a proximal end of the rasp main body. A first tangential plane of the lateral side of the outer contour in the region of the indentation and a second tangential plane on a rasp body part contact surface, defined by the rasp body part receptacle and facing away from the rasp main body, in the region of the distal end of the rasp body part receptacle include an indentation angle which is less than 85°.

In a second aspect of the invention, a modular prosthesis rasp comprises a rasp body having a rasp main body and at least one modular rasp body part connectable to the rasp main body. The rasp main body comprises a rasp body part receptacle for receiving the at least one rasp body part in a connected position in which the rasp main body and the at least one rasp body part are connected to each other, and in which the rasp body defines an outer contour defined partly by the rasp main body and partly by the at least one rasp body part. The rasp body part receptacle extends from an indentation, defining a distal end of the rasp body part receptacle, on a lateral side of the rasp main body to a proximal end of the rasp main body. A cross-sectional area of the rasp main body perpendicular to a longitudinal axis of the rasp main body, starting from the distal end of the rasp body part receptacle, decreases in the direction towards a proximal end of the rasp main body up to a minimum and increases again from the minimum up to the proximal end.

In a third aspect of the invention, a modular prosthesis rasp comprises a rasp body having a rasp main body and at least one modular rasp body part connectable to the rasp main body. The rasp main body comprises a rasp body part receptacle for receiving the at least one rasp body part in a connected position in which the rasp main body and the at least one rasp body part are connected to each other, and in which the rasp body defines an outer contour defined partly by the rasp main body and partly by the at least one rasp body part. The rasp body part receptacle extends from an indentation, defining a distal end of the rasp body part receptacle, on a lateral side of the rasp main body to a proximal end of the rasp main body. Furthermore, a connecting device is provided for releasably connecting the rasp main body and the at least one rasp body part in the connected position. The connecting device comprises first and second connecting elements, which are arranged or formed, on the one hand, on the rasp main body and, on the other hand, on the at least one rasp body part and are in engagement with each other in the connected position. The rasp main body comprises a female or substantially female connecting element, and the at least one rasp body part comprises a corresponding male or substantially male connecting element.

BRIEF DESCRIPTION OF THE DRAWING FIGURES

The foregoing summary and the following description may be better understood in conjunction with the drawing figures, of which.

DETAILED DESCRIPTION OF THE INVENTION

Although the invention is illustrated and described herein with reference to specific embodiments, the invention is not intended to be limited to the details shown. Rather, various modifications may be made in the details within the scope and range of equivalents of the claims and without departing from the invention.

The invention relates to a modular prosthesis rasp with a rasp body comprising a rasp main body and at least one modular rasp body part connectable to the rasp main body, the rasp main body comprising a rasp body part receptacle for receiving the at least one rasp body part in a connected position in which the rasp main body and the at least one rasp body part are connected to each other, and in which the rasp body defines an outer contour defined partly by the rasp main body and partly by the at least one rasp body part, the rasp body part receptacle extending from an indentation, defining a distal end of the rasp body part receptacle, on a lateral side of the rasp main body to a proximal end of the rasp main body, a first tangential plane of the lateral side of the outer contour in the region of the indentation and a second tangential plane at a rasp body part contact surface, defined by the rasp body part receptacle and facing away from the rasp main body, in the region of the distal end of the rasp body part receptacle including an indentation angle which is less than 85°.

An indentation angle which is less than 85° makes it possible to form the rasp body part receptacle in a such way that during insertion, in particular, into the medullary cavity of a femur for preparation of a cavity for a hip joint endoprosthesis stem, the rasp main body can no longer come into contact with the trochanter. Undesired injury not only to the trochanter, but also to surrounding soft tissue is thereby prevented. The rasp body part receptacle thus forms a lateral recess which, on the one hand, significantly reduces traumatization of soft tissue and bones and, on the other hand, enables optimum positioning of the actual implant with little effort.

Expediently, the indentation angle has a value ranging from 20° to 70°. It is expedient if the value ranges from 35° to 55°. Preferably, the indentation angle is approximately 45°. An indentation angle with values in the given ranges enables formation of a stable rasp main body and, in addition, a rasp body part receptacle which allows insertion of the rasp main body into the bone cavity without damaging soft tissue or the trochanter.

Furthermore, it is expedient if the rasp body part contact surface defines a continuous or substantially continuous surface. In particular, this means that this surface does not have any kinks and, within the meaning of a mathematical definition, is not only continuous, but also differentiable.

To enable a particularly stable prosthesis rasp to be constructed, in particular, when the rasp main body and the modular rasp body part assume the connected position, it is advantageous if the at least one rasp body part has a rasp main body contact surface, which in the connected position lies with surface-to-surface contact or substantially with surface-to-surface contact against the rasp body part contact surface. A particularly good support is achieved by the rasp body part lying against the rasp main body with surface-to-surface contact or substantially with surface-to-surface contact.

The manufacture of the prosthesis rasp can be easily simplified by the rasp body part contact surface having a plane or substantially plane first rasp body part contact surface region.

The prosthesis rasp is even easier to manufacture if the first rasp body part contact surface region extends towards a proximal end of the rasp body part receptacle. In particular, it can extend all the way to the proximal end of the rasp body part receptacle.

It is expedient if the first rasp body part contact surface region and a longitudinal axis of the rasp main body define an angle of inclination which has a value ranging from 0° to 25°. Preferably, the angle of inclination ranges from 0° to 10°. It is particularly advantageous if the angle of inclination is approximately 5°. The risk of contact between the rasp main body and the trochanter as well as surrounding soft tissue when inserting the rasp main body into the medullary cavity of the femur can be further reduced by providing an angle of inclination in the given ranges. In particular, the angle of inclination between the longitudinal axis and the first rasp body part contact surface region can be defined if the rasp body part contact surface region is inclined, starting from its distal end, in the medial direction, i.e., in particular, if a distance of the first rasp body part contact surface region from a lateral side face of the rasp body increases in the proximal direction, i.e., towards the proximal end of the rasp body.

The insertion of the rasp main body into the cavity of the femur can be even further improved by the rasp body part contact surface having a second rasp body part contact surface region which is continuously curved. Preferably, the second rasp body part contact surface region passes in the mathematical sense continuously into the first rasp body part contact surface region adjoining it proximally.

The rasp main body can be manufactured particularly easily if the second rasp body part contact surface region has a constant or substantially constant radius of curvature. For example, it can thus be prepared with a simple rotating metalworking tool, for example, a milling tool.

It is expedient if the radius of curvature has a value ranging from 5 mm to 25 mm. The stability of the rasp main body can be further improved by, for example, the radius of curvature having a value ranging from 10 mm to 20 mm.

The rasp main body can be inserted into a cavity of a femur in a particularly easy way if the second rasp body part contact surface region extends as far as the distal end of the rasp body part receptacle. In particular, it is advantageous for the manufacture of the prosthesis rasp if a distal section of the second rasp body part contact surface region that extends as far as the distal end of the rasp body part receptacle is of plane or substantially plane construction. For example, a curved section of the second rasp body part contact surface region can then be formed between this plane section and the first rasp body part contact surface region.

The rasp main body can be manufactured particularly easily if two side faces, facing away from each other, of a first pair of side faces of the rasp main body extend parallel or substantially parallel to each other. Alternatively, it may also be expedient if these are inclined slightly to each other so that in the distal direction a distance between them decreases.

It is expedient if the two side faces of the first pair of side faces are plane or substantially plane. The respective faces can then be produced particularly easily.

In accordance with a further preferred embodiment of the invention, it may be provided that two side faces, facing away from each other, of a second pair of side faces of the rasp main body are at least partly of plane construction, and their plane regions are inclined to each other about a stem angle, which stem angle has a value ranging from 0° to 15°. Preferably, the stem angle has a value ranging from 0° to 8°. Preferably, lateral and medial side faces are inclined relative to each other about the stem angle. In this way, an optimized fixing of the prosthesis stem in the bone cavity to be prepared can be achieved, namely by means of a conical clamping or a press fit.

The manufacture of the rasp main body can be further simplified by, for example, the two side faces of the second pair of side faces being plane or substantially plane, starting from the indentation to a distal end region of the rasp main body. For example, it is thus also possible for a medial side face, starting from the indentation, to be curved in the proximal direction and thus conform optimally to a natural cavity of the bone.

The prosthesis rasp can be manufactured particularly easily if the two side faces of the second pair of side faces are completely plane or substantially plane.

To form a cavity which offers a prosthesis stem excellent hold by clamping or press fit, it is expedient if a cross-sectional area of the rasp main body perpendicular to a longitudinal axis of the rasp main body, starting from the distal end of the rasp body part receptacle, decreases in the direction towards a distal end of the rasp main body.

It is, in particular, advantageous if, in a prosthesis rasp of the kind described at the outset, a cross-sectional area of the rasp main body perpendicular to a longitudinal axis of the rasp main body, starting from the distal end of the rasp body part receptacle, decreases in the direction towards a distal end of the rasp main body. A perfect press fit of the actual prosthesis stem in the prepared bone cavity can thus be ensured in a simple and secure way.

It is advantageous if a cross-sectional area of the rasp main body perpendicular to a longitudinal axis of the rasp main body, starting from the distal end of the rasp body part receptacle, decreases in the direction towards a proximal end of the rasp main body up to a minimum and increases again from the minimum up to the proximal end. This special shape of a proximal end region of the rasp main body makes it possible to construct it in such a way that when inserting it into the medullary cavity of the femur, soft tissue and the trochanter are not damaged.

Furthermore, it may be expedient if, in a prosthesis rasp of the kind described at the outset, a cross-sectional area of the rasp main body perpendicular to a longitudinal axis of the rasp main body, starting from the distal end of the rasp body part receptacle, decreases in the direction towards a proximal end of the rasp main body up to a minimum and increases again from the minimum up to the proximal end. In an analogous manner to that described above, this design of the rasp main body makes it possible to insert it into a bone cavity of a femur without or essentially without traumatization of surrounding soft tissue or of the trochanter.

In accordance with a further preferred embodiment of the invention, it may be provided that a function of the cross-sectional area of the rasp main body perpendicular to the longitudinal axis, starting from the distal end of the rasp body part receptacle in the direction towards a proximal end of the rasp main body, forms, in dependence upon the distance of the cutting plane defining the cross-sectional area from the distal end of the rasp body part receptacle, a mathematically continuous function. Preferably, this is a continuous and differentiable function, i.e., which does not have any kinks or jumps. Such a function preferably has a curve to the right, which corresponds to a positive value of the second derivative of the function.

It is particularly expedient if the minimum is at a distance from the distal end of the rasp body part receptacle, which corresponds to at least 0.1 times a length of the rasp body part receptacle parallel to the longitudinal axis. Such a distance ensures that there is a smooth indentation of the rasp body part receptacle, which makes it possible to avoid injury to surrounding soft tissue and the trochanter when inserting the rasp main body into the medullary cavity of the bone.

Furthermore, it may also be advantageous if the distance corresponds to at least 0.2 times the length of the rasp body part receptacle. Moreover, it is expedient if the distance corresponds to at least 0.3 times the length of the rasp body part receptacle. In preferred embodiments, the minimum may be at a distance from the distal end of the rasp body part receptacle, which corresponds approximately to 0.4 to 0.5 times the length of the rasp body part receptacle. Provision of the minimum approximately in the middle region of the rasp body part receptacle makes, in particular, an even further improved shape possible, which independently of a position of the rasp main body during the introduction, i.e., during the insertion into the medullary cavity of the femur is at a distance which is necessary in order to avoid traumatization of the trochanter and surrounding soft tissue.

To avoid injury during insertion of the rasp stem into the bone cavity, it is expedient if the rasp main body has a distal end which forms a blunt tip.

In order to give the medullary cavity of the bone a shape which is optimally suited for receiving the prosthesis stem, it is advantageous if one or more side faces of the rasp main body and/or of the at least one rasp body part are provided at least partly with rasp teeth for machining the bone. Preferably, the rasp body part contact surface and the rasp main body contact surface are free of rasp teeth. For optimized machining it is, furthermore, expedient if all side faces which define the outer contour of the rasp body are provided with rasp teeth. The distal end of the rasp main body is preferably free of rasp teeth so as not to injure or expand in an undesired way the medullary cavity and, in particular, the cortex, when inserting the rasp main body into the medullary cavity.

To improve handling of the prosthesis rasp, it is advantageous if a coupling element for releasable connection to a rasp grip is arranged or formed on the rasp main body in the region of its proximal end. The coupling element may be of male or female configuration. The prosthesis rasp can be manipulated in a desired way by means of a rasp grip in order to prepare the bone cavity.

Furthermore, it is expedient if a coupling element for releasable connection to a handle is arranged or formed on the at least one rasp body part in the region of its proximal end. For example, after insertion of the rasp main body into the bone cavity, the rasp body part can thus be inserted in a second step independently of the rasp main body and, for example, connected to the rasp main body in order to prepare the cavity in the bone, in particular, in the region of the trochanter in the desired way.

In accordance with a further preferred embodiment of the invention, a connecting device may be provided for releasably connecting the rasp main body and the at least one rasp body part in the connected position. The connecting device makes it possible to specifically connect the rasp main body and the least one rasp body part to each other easily and securely.

The connecting device can be constructed in a simple way if it comprises first and second connecting elements which are arranged or formed, on the one hand, on the rasp main body and, on the other hand, on the at least one rasp body part and are in engagement with each other in the connected position. In particular, the connecting elements may be constructed for formation of a connection of the rasp main body and the at least one rasp body part to each other with force locking and/or positive locking.

It is advantageous if the rasp main body comprises a female or substantially female connecting element and if the at least one rasp body part comprises a corresponding male or substantially male connecting element. This configuration has, in particular, the advantage that no or essentially no parts of the rasp body part contact surface of the rasp main body protrude or need to protrude, which may lead in an undesired way to traumatization of the surrounding soft tissue or of the trochanter when inserting the rasp main body into the medullary cavity of the bone. Expediently, the female connecting element is configured in the form of a recess and the male connecting element in the form of a corresponding projection. In particular, it is advantageous if the two connecting elements engage with each other with positive locking or at least partly with positive locking in the connected position, whereby a defined and secure connection can be made between the rasp main body and the at least one rasp body part.

In accordance with a further preferred embodiment of the invention, it may be advantageous in a prosthesis rasp of the kind described at the outset if a connecting device is provided for releasably connecting the rasp main body and the at least one rasp body part in the connected position, if the connecting device comprises first and second connecting elements, which are arranged or formed, on the one hand, on the rasp main body and, on the other hand, on the at least one rasp body part and are in engagement with each other in the connected position, if the rasp main body comprises a female or substantially female connecting element, and if the at least one rasp body part comprises a corresponding male or substantially male connecting element. Construction of a prosthesis rasp in this way has, in particular, the advantage that no parts, in particular, no connecting elements, need protrude from the rasp body part receptacle in the direction towards the at least one rasp body part in order to connect the rasp main body and the at least one rasp body part. In particular, if the rasp body part receptacle defines a rasp body part contact surface facing away from the rasp main body, it can be constructed without any projections. This is also particularly expedient in precisely this region as contact with surrounding soft tissue and also with the trochanter when inserting the rasp main body into the medullary cavity of the bone to be machined can thus be easily avoided.

The connecting device can be particularly easily manufactured if the female connecting element comprises a bore or a blind hole. For example, the male connecting element may then be configured in the form of a corresponding projection or pin, which is insertable, in particular, slidable, with positive locking into the female connecting element. Preferably, the connecting device is so constructed that the main body and the at least one rasp body part can be brought into engagement with each other by a displacement relative to each other parallel to an axis defined by at least one of the connecting elements.

In order that the at least one rasp body part can be held in a defined and secure way on the rasp main body, it is expedient if the female connecting element has a lateral guide slot which extends as far as the rasp body part contact surface; for example, the male connecting element of the at least one rasp body part can thus pass through the guide slot and with a projecting section engage, in particular, an undercut formed by the female connecting element in order to thus hold the at least one rasp body part in the connected position on the rasp main body.

To ensure that the at least one rasp body part and the rasp main body cannot become detached from each other in an undesired way, it is advantageous if a securing device is provided for securing a connection of the rasp main body and the at least one rasp body part in the connected position.

The securing device can be manufactured in a simple way if it comprises first and second securing elements which are arranged or formed, on the one hand, on the rasp main body and, on the other hand, on the at least one rasp body part and are in engagement with each other in a securing position. In the securing position, the first and second securing elements are therefore in engagement with each other and also the male and female connecting elements which assume the connected position.

To enable a particularly compact prosthesis rasp to be constructed, it is expedient if the first securing element is arranged or formed on or in the region of the female connecting element, and if the second securing element is arranged or formed on or in the region of the male connecting element. For example, a securing element can be configured in the form of a recess and the corresponding other securing element in the form of a projection, the securing elements preferably being arranged or formed for movement relative to each other, in order to be able to be easily made to engage with each other and disengage from each other again.

For the handling of the prosthesis rasp it is, in particular, advantageous if the securing device is configured in the form of a latching connection device, and if the first and second securing elements are configured in the form of latching elements which engage with each other in a latching manner in the securing position. A latching connection device makes it possible, in particular, to automatically secure the rasp main body and the at least one rasp body part in the connected position as the connecting elements can enter into engagement in a latching manner with each other when the rasp main body and the at least one rasp body part are transferred to the connected position. In this case, a latching projection is preferably provided, which can engage in a latching recess in the securing position. The latching projection is advantageously movably mounted on the at least one rasp body part or on the rasp main body. Furthermore, it may be provided to resiliently bias the first and second securing elements in relation to each other, so that, for example, in the event of deflection from the securing position they can automatically go back into it.

It is advantageous if the rasp main body and the at least one rasp body part are movable relative to each other in the connected position. This configuration makes it possible to use the connecting device, in particular, also as guide device, in order to guide in a specific manner a relative movement of the at least one rasp body part and the rasp main body.

In order to construct the rasp body part receptacle in a way which is large enough to avoid contact between the rasp body part contact surface and the trochanter, it is expedient if the second tangential plane and the first rasp body part contact surface region form an obtuse included angle.

Preferably, the obtuse included angle has a value ranging from 95° to 160°. Furthermore, it may be expedient if the obtuse included angle has a value ranging from 105° to 150°.

When inserting the rasp main body into the medullary cavity of a bone, in particular, a femur, the rasp main body may be successively pivoted relative to the bone. In particular, its lateral proximal end region can be pivoted in the direction towards the trochanter if a distal end region of the rasp main body is configured in the form of an elongate stem of straight-line configuration. To ensure that surrounding soft tissue and the trochanter region are not injured when inserting the rasp main body, it is expedient if a length of the first rasp body part contact surface region parallel or substantially parallel to a longitudinal axis of the rasp main body corresponds approximately to 0.4 times to 0.75 times the length of the rasp body part receptacle. Preferably, the value ranges from 0.6 to 0.7. Particularly preferred is a length ratio ranging from 0.62 to 0.66.

In accordance with a further preferred embodiment of the invention, it may be advantageous if the cross-sectional area of the rasp main body in the minimum has a value which corresponds to 0.5 times to 0.8 times the cross-sectional area in the region of the indentation. It is particularly advantageous if the cross-sectional area in the region of the minimum corresponds to 0.62 times to 0.7 times the cross-sectional area in the region of the indentation. These cross-sectional area ratios make it possible, in particular, to give the rasp body part receptacle a shape which enables insertion of the rasp main body into the bone to be machined without injuring the trochanter.

In order to minimize traumatization of surrounding soft tissue when inserting the rasp main body into the medullary cavity of the bone, it is advantageous if the rasp body part contact surface and side faces of the rasp main body adjoining it have at least partly rounded edges. In particular, the rasp body part contact surface may also have a convex outer contour facing away from the rasp main body.

The prosthesis rasp can be made particularly stable by the rasp main body and/or the at least one rasp body part each being constructed in one piece.

The handling of the prosthesis rasp can be enhanced, in particular, by a rasp grip which is releasably connectable to the rasp main body being provided.

The rasp grip can be connected to the rasp main body in a simple way, in particular, if a coupling device is provided for releasably coupling the rasp grip to the rasp main body, which coupling device comprises on the rasp grip and on the rasp main body first and second coupling elements which can be brought into engagement in a coupling position. The coupling elements may be constructed, in particular, so as to be in engagement with force locking and/or positive locking in the coupling position. In particular, projections and recesses corresponding to each other, which may be selectively arranged or formed on the rasp main body and on the rasp grip, are conceivable.

For further improvement of the handling of the prosthesis rasp, it is advantageous if it comprises a handle which is releasably connectable to the at least one rasp body part. Depending on the design of the rasp grip, this may optionally also form the handle, so that it can be selectively connected to the rasp main body and to the at least one rasp body part. The handle preferably comprises a coupling element corresponding to the coupling element of the at least one rasp body part.

In order to be able to machine in the desired way, in particular, the trochanter after insertion of the rasp main body into the medullary cavity of the bone, it is expedient if the prosthesis rasp comprises a chisel part releasably connectable to the rasp main body. Preferably, the chisel part can be brought into engagement with the rasp main body and then still moved relative to it, so that a precisely defined preparation of the trochanter is possible with the chisel part.

It is advantageous if the chisel part comprises at least a third connecting element which can be at least partly brought into engagement with the connecting element arranged or formed on the rasp main body. In particular, the third connecting element may be constructed so as to be brought into engagement with the female connecting element of the rasp main body. For example, it may, if the female connecting element is constructed in the form of a bore or a blind hole, be constructed in the form of a corresponding bar-shaped projection.

Advantageously, the connecting element comprised by the rasp main body forms a guide for the third connecting element for guiding movement of the chisel part relative to the rasp main body. If the rasp main body is first brought into its desired form in the medullary cavity of the bone, the chisel part can then be guided in a defined manner relative to the rasp main body, for example, in order pre-machine the trochanter prior to preparation with the at least one rasp body part.

To improve the handling of the chisel part, it is expedient if it comprises at least one coupling element, in particular, for connection to a handle. In particular, the coupling element may be constructed so as to be connected to the handle connectable to the at least one rasp body part. In this way, the number of handles required for handling the prosthesis rasp can be minimized.

In order that machining, in particular, of the trochanter with the chisel part can be carried out in a particularly defined manner, it is expedient if a stop is provided for delimiting movement of the chisel part relative to the rasp main body. In particular, the stop may serve to delimit movement of the chisel part relative to the rasp main body in the distal direction.

The stop can be constructed in a simple way if a proximal end of the rasp main body forms it. The rasp main body can then be inserted in the desired way into the medullary cavity of the bone and the chisel part brought up to the proximal end of the rasp main body, and bone, in particular, the trochanter, can be machined during this movement.

Figure 1:
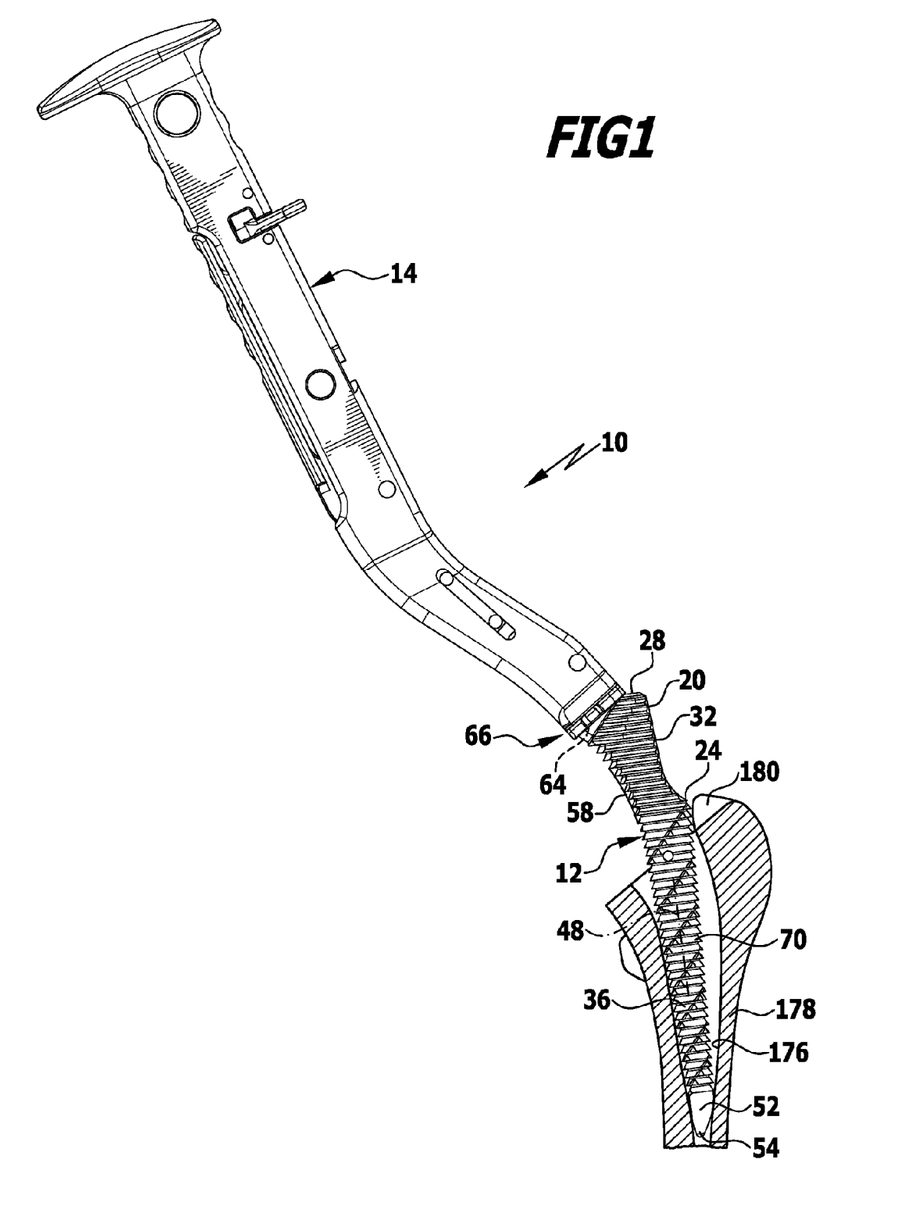
FIG. 1: shows a diagrammatic general view of part of a prosthesis rasp when being inserted into the medullary cavity of a femur.
Figure 2:
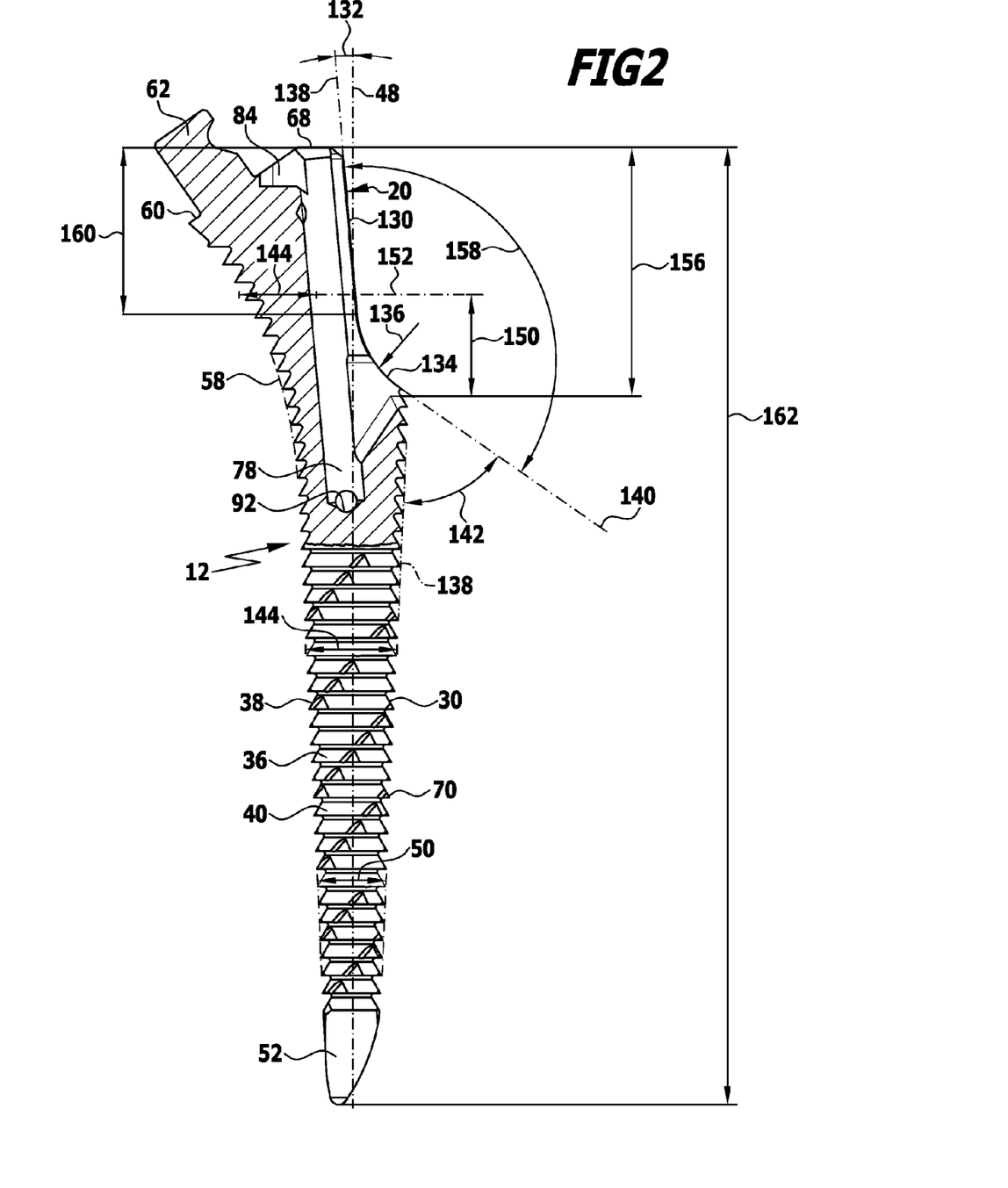
FIG. 2: shows a partly sectional side view of a rasp main body of the prosthesis rasp.
Figure 3:
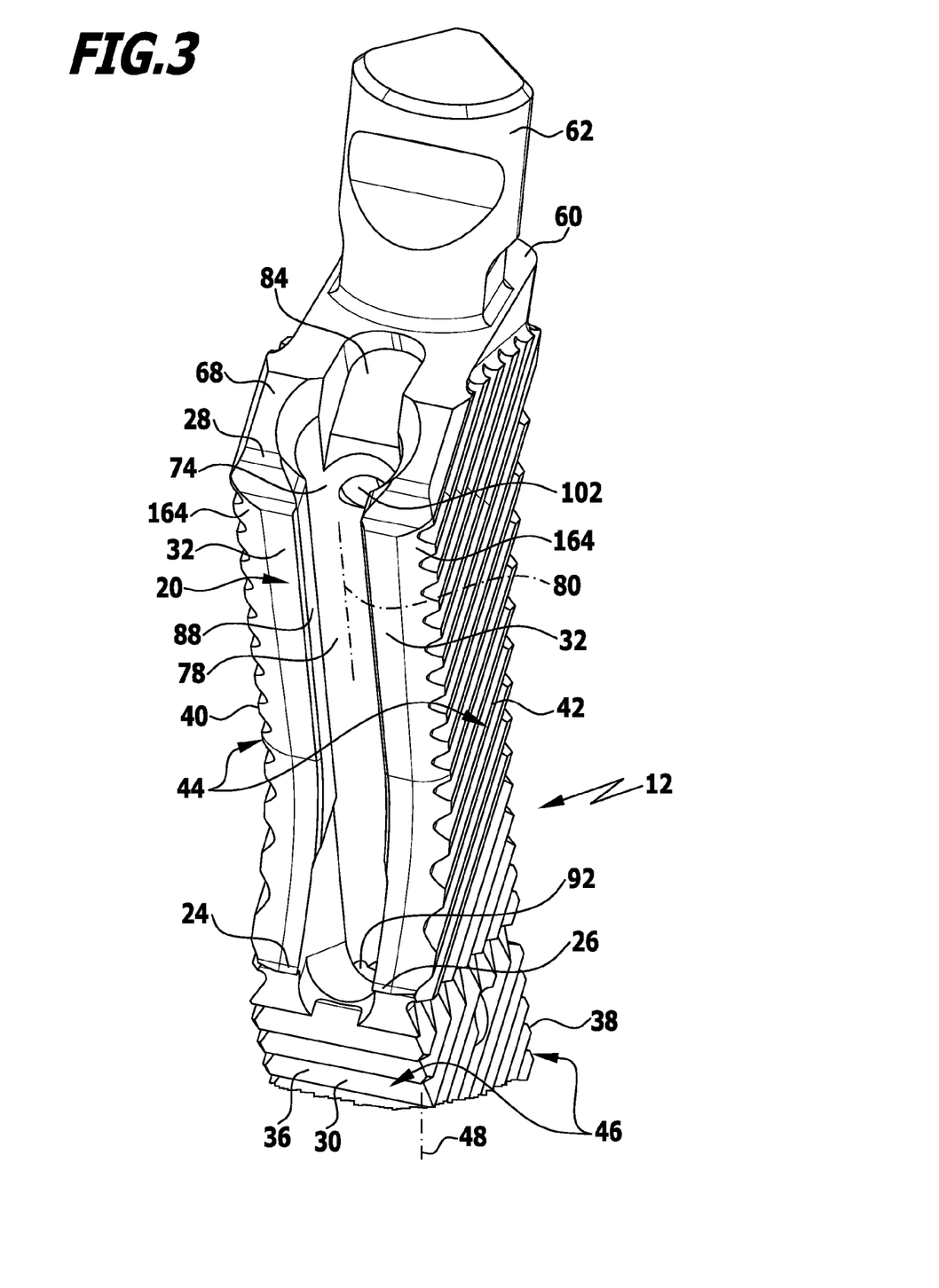
FIG. 3: shows a perspective partial view of a proximal end region of the rasp main body.
Figure 4:
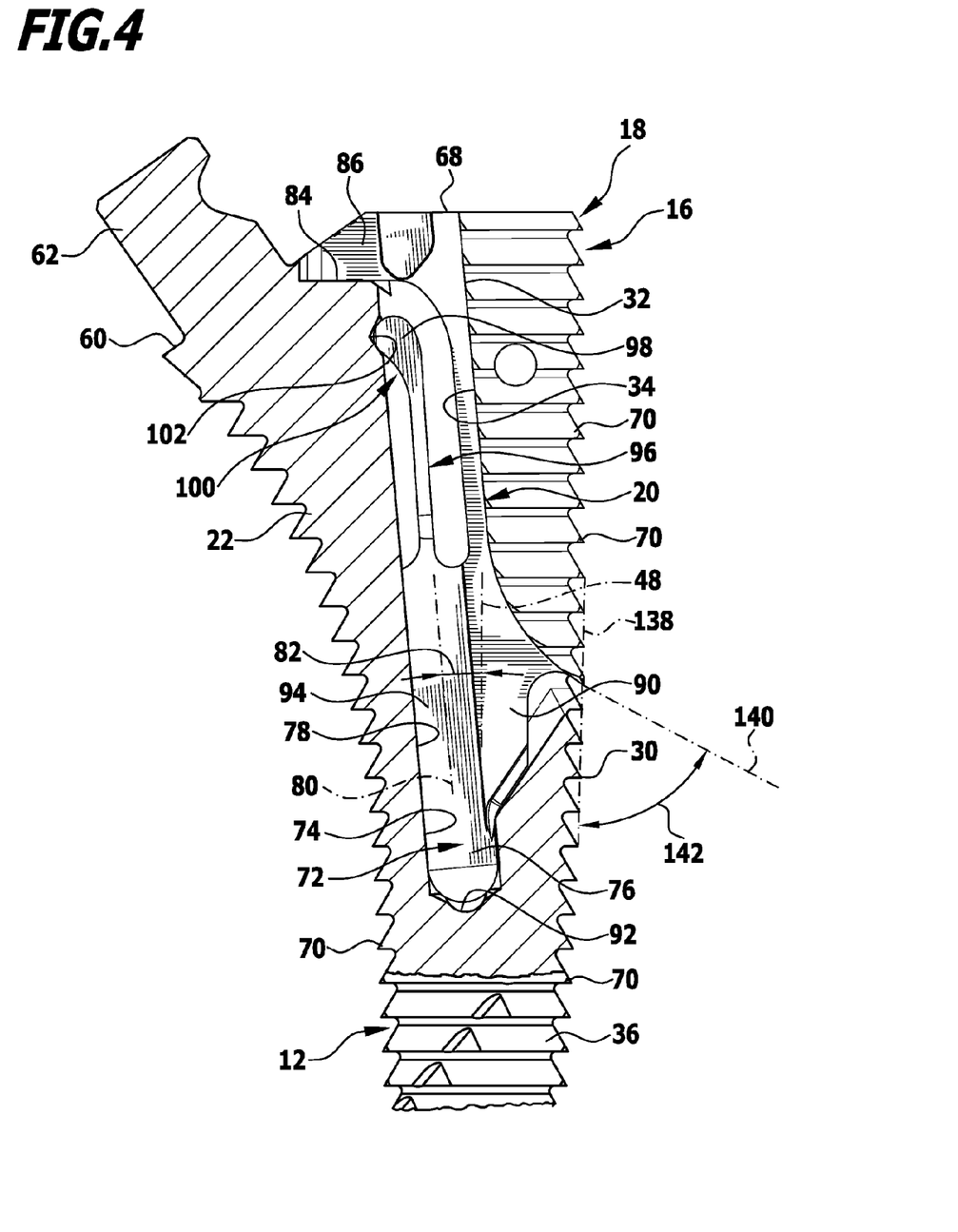
FIG. 4: shows a partially sectional side view of a proximal end region of the rasp main body with the rasp body part coupled to it.

A first embodiment of a modular prosthesis rasp generally designated by reference numeral 10 is diagrammatically represented in FIG. 1. It comprises a rasp main body 12 and a rasp grip 14 releasably connectable thereto. The prosthesis rasp 10 further comprises a rasp body part 16, which is releasably connectable to the rasp main body 12, and, in a connected position, as shown, by way of example, in FIG. 4, forms together with the rasp main body 12 a rasp body 18.

The rasp main body 12 comprises a rasp body part receptacle 20 for receiving the rasp body part 16 in the connected position. In this, the rasp main body 12 and the rasp body part 16 each partially define an outer contour 22 of the rasp body 18.

Starting from an indentation 26, defining a distal end 24 of the rasp body part receptacle 20, on a lateral side face 30 of the rasp main body 12, the rasp body part receptacle 20 extends as far as a proximal end 28 of the rasp main body 12. The rasp body part receptacle 20 is open at the sides, i.e., facing in the anterior and posterior directions, and proximally, so that the rasp body part 16 fills out the rasp body part receptacle 20 completely. A boundary surface, facing away from the rasp main body 12, of the rasp body part receptacle 20 defines a rasp body part contact surface 32 against which the rasp body part 16 lies with a corresponding rasp main body contact surface 34 with surface-to-surface contact or substantially with surface-to-surface contact.

Distally of the indentation 26, the rasp main body 12 is configured in the form of a stem 36 with four plane side faces 30, 38, 40 and 42, with the side faces 40 and 42 forming a first pair 44 of side faces of the rasp main body 12, which extend at a slight incline to each other and towards each other in the distal direction. The side faces 30 and 38 are, like the side faces 40 and 42, plane and form a second pair 46 of side faces. The side faces 30 and 38 are also inclined in relation to a longitudinal axis 48 of the stem 36 and, therefore, also relative to each other, more specifically, at a stem angle 50 having a value of approximately 7°. Alternatively, stem angles 50 ranging from 0° to 15° are also conceivable. The side faces 30 and 38 are plane essentially as far as a distal end region 52 of the rasp main body 12. All in all, a conical stem 36 is thus formed.

The distal end region 52 defines a distal end 54 of the stem 36 in the form of a blunt tip 56. This is convexly curved, in particular, laterally, facing away from the rasp main body 12.

The medial side face 38 is plane up to approximately the level of the indentation 26, and, starting from this, is curved slightly in the medial direction, so that a concave curvature 58 facing away from the rasp main body 12 is defined. There protrudes from a medial end face 60 inclined slightly in the medial direction a coupling pin 62 which forms a coupling element and can engage in a coupling receptacle 64, not shown in detail in the Figures, which also defines a coupling element of a coupling device 66 for releasably coupling the rasp grip 14 to the rasp main body 12, in order to connect the rasp main body 12 to the rasp grip 14.

Figure 6:
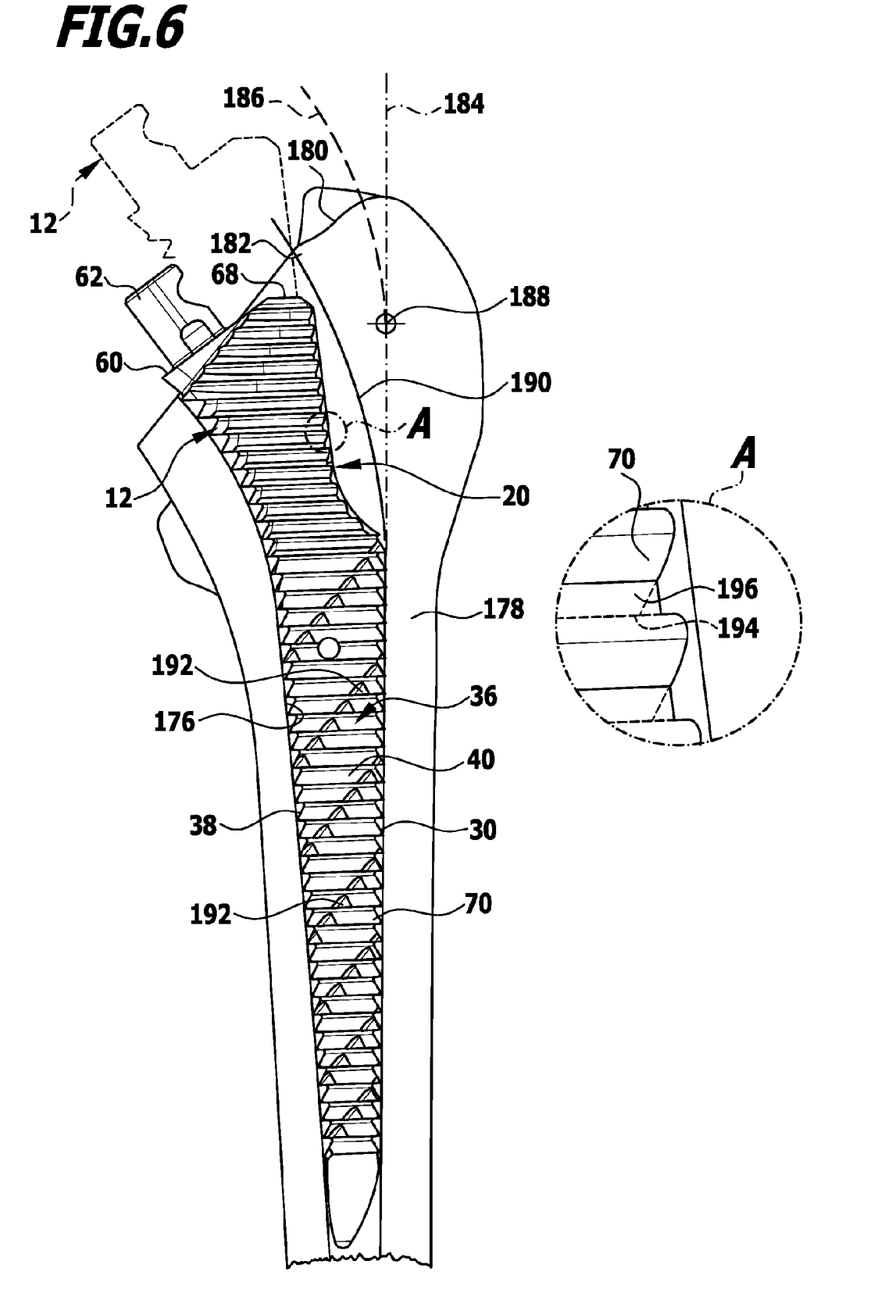
FIG. 6: shows a side view of the rasp main body inserted into the medullary cavity of the femur with path curves of various rasp main bodies when being inserted into the medullary cavity.

The outer contour 22 defines a proximal end face 68 of the rasp body 18, which is inclined at approximately 40° to the end face 60 and extends transversely to the longitudinal axis 48. Both the rasp main body 12 and the rasp body part 16 are provided with rasp teeth 70 on their outer surfaces, but not on the rasp body part contact surface 32 or the rasp main body contact surface 34. Also free of rasp teeth are the tip 56 and the end faces 60 and 68. As is easy to recognize, in particular, in FIG. 6, the rasp teeth 70, but only of the side faces 40 and 42, are interrupted distally of the indentation 26 by a total of seven so-called chip-breaking grooves 192 which extend parallel to each other, but at an incline of approximately 45° relative to the longitudinal axis 48. They serve to reduce the pressure in the medullary cavity 176 while it is being prepared. Furthermore, the rasp teeth 70, but only of the side faces 40 and 42, are of atraumatic construction proximally of the indentation 26. As is easy to recognize in the enlarged detail view A in FIG. 6, cutting edges 194, drawn in broken lines in the enlarged detail view A, of the rasp teeth 70 of the side faces 40 and 42 are removed proximally of the indentation 26, so that the rasp teeth 70 have end faces 196 extending approximately parallel to the respective side faces 40 and 42. The number of chip-breaking grooves 192 varies in dependence upon a size of the rasp main body 12. Fewer chip-breaking grooves 192 are provided in small rasp main bodies 12 than in large rasp main bodies 12.

A connecting device 72 comprising a female connecting element 74 and a male connecting element 76, which are engageable with each other with positive locking, serves for releasable connection of the rasp main body 12 and the rasp body part 16. The female connecting element 74 is configured in the form of a blind hole bore 78 extending from the proximal end 28 into the stem 36 somewhat beyond the indentation 26 in the distal direction. A longitudinal axis 80 of the blind hole bore 78 is inclined at an angle 82 of approximately 5° relative to the longitudinal axis 48. In the region of its proximal end, the blind hole bore 78 is medially extended by a recess 84 in which a corresponding projection 86 of the rasp body part 16 engages essentially with positive locking in the connected position.

The blind hole bore 78 is open towards the rasp body part contact surface 32 via a lateral guide slot 88, through which, in the connected position, a holding region 90 of the rasp body part 16 passes, which carries the male connecting element 76. The latter is essentially configured as a pin-shaped pin region 94 and extends in this shape over approximately half of the length of the blind hole bore 78, starting from its distal end 92.

Formed integrally with the pin region 94 of the male connecting element 76 is a spring section 96 which extends parallel to the longitudinal axis 80, facing in the proximal direction. It carries at its proximal end a securing projection 98 protruding somewhat in the medial direction and forming part of a securing device generally designated by reference numeral 100. The securing projection 98 is thus arranged on the connecting element 76 or comprised by it. A further securing element in the form of a securing recess 102 is formed somewhat distally of the recess 84 on the blind hole bore 78 and faces in the lateral direction. When the male connecting element is brought with its pin region 94 up to the end 92, the securing projection 98 resiliently biased by the spring section 96 can enter the securing recess 102 and in this way automatically secure the rasp body part 16 in the connected position on the rasp main body 12. The prosthesis rasp then assumes the secured position shown in FIG. 4. The securing device 100 is, in addition, so configured that the securing projection 98 engages the securing recess 102 when the projection 86 enters the recess 84.

The rasp body part 16 further comprises a coupling element 104 in the form of a coupling recess which can be made to engage with a corresponding coupling projection 106 of a handle 108 in order to bring the rasp body part 16 up to and connect it to the rasp main body 12.

The prosthesis rasp 10 further comprises a box chisel 110 which forms a chisel part which is connectable to the rasp main body 12. The box chisel 110 comprises a substantially cube-shaped chisel body 112 which has a cutting edge 114 in the area of transition between a distal end face 116 and a lateral side face 118 for machining bone. The proximal end 28 of the rasp main body 12 thus forms a stop 166 for delimiting movement of the box chisel 110 relative to the rasp main body 12 in the distal direction.

Protruding from the end face 116 and facing in the proximal direction is a coupling pin 120, which is configured so as to correspond to the blind hole bore 78 and coming from the proximal direction with its distal end 122 foremost is insertable therein. Formed on the chisel body 112 and facing in the proximal direction is a coupling recess 124 which can be made to engage with a corresponding coupling projection 126 of a handle 128. This enables the box chisel 110 to be easily and safely handled and, in particular, coupled to the rasp main body 12 in a machining position.

The following describes the rasp body part receptacle again in greater detail.

The rasp body part contact surface 32 comprises a first rasp body part contact surface region 130 which is plane or substantially plane. It extends as far as the proximal end 28 of the rasp body part receptacle 20. The first rasp body part contact surface region 130 and the longitudinal axis 48 of the rasp main body 12 define between them an angle of inclination 132 of approximately 5°. This may selectively also range from 0° to 25°.

The rasp body part contact surface 32 further comprises a second rasp body part contact surface region 134 which is continuously curved. This has, in the embodiment shown in the Figures, a constant or substantially constant radius of curvature 136 ranging from 10 mm to 20 mm. The second rasp body part contact surface region 134 extends as far as the distal end 24 of the rasp body part receptacle 20. The outer contour 22 defines in the region of the indentation 26 a first tangential plane 138. A second tangential plane 140 is defined by a plane lying at the rasp body part contact surface 32, facing away from the rasp main body 12, in the region of the distal end 24 of the rasp body part receptacle 20. The tangential planes 138 and 140 define between them an indentation angle 142 which is less than 85°. In the embodiment shown in the Figures, the indentation angle 142 is approximately 60°.

All in all, a continuous or substantially continuous surface is thus defined, namely the rasp body part contact surface 32, which is only interrupted by the guide slot 88. Here, continuous means, in particular, mathematically continuous, so that the first rasp body part contact surface region 130 continues without a kink or jump into the second rasp body part contact surface region 134.

A cross-sectional area 144 of the rasp main body 12 perpendicular to the longitudinal axis 48 thereof, starting from the distal end 24 of the rasp body part receptacle 20, decreases in the direction towards the distal end 54.

However, a cross-sectional area 144 of the rasp main body 12 perpendicular to the longitudinal axis 48 thereof, starting from the distal end 24 of the rasp body part receptacle 20, also decreases in the direction towards the proximal end 28 of the rasp main body 12 up to a minimum 146 and increases again from the minimum 146 to the proximal end 28. A function 148 of the standardized cross-sectional area 144 of the rasp main body 12 in dependence upon a distance 150 from the distal end 24 is designated by 148 in FIG. 9. As is recognizable in FIG. 9, the function 148 of the cross-sectional area 144 of the rasp main body 12 perpendicular to the longitudinal axis 48, starting from the distal end 24 of the rasp body part receptacle 20 in the direction towards the proximal end 28 of the rasp main body, forms, in dependence upon the distance 150 of a cutting plane 152 defining the respective cross-sectional area 144 from the distal end 24 of the rasp body part receptacle 20, a mathematically continuous function. Mathematically continuous means that the function is derivable and no jumps of the derived function occur. The minimum 146 is at a distance 154 from the distal end 24 of the rasp body part receptacle 20. This distance 154 corresponds at least to 0.1 times a length 156 of the rasp body part receptacle 20 parallel to the longitudinal axis. In the embodiment shown the Figures, the distance 154 has a value corresponding approximately at least to 0.3 times the length 156.

Furthermore, the second tangential plane 140 and the first rasp body part contact surface region 32 form an obtuse included angle 158. This has a value ranging from 95° to 160°, preferably 105° to 150°. In the embodiment shown in the Figures, the included angle 158 is approximately 125°.

A length 160 of the first rasp body part contact surface region 130 parallel or substantially parallel to the longitudinal axis 48 of the rasp main body 12 corresponds approximately to 0.4 times to 0.75 times the length 156 of the rasp body part receptacle 20. Preferably, the length 160 corresponds approximately to 0.6 to 0.7 times the length 156. In the embodiment shown in the Figures, the length 160 corresponds approximately to 0.6 times the length 156.

Furthermore, the length 156 of the rasp body part receptacle 20 parallel or substantially parallel to the longitudinal axis 48 of the rasp main body 12 corresponds approximately to 0.15 to 0.4 times a total length 162 of the rasp main body 12. Preferably, the length 156 corresponds approximately to 0.25 to approximately 0.3 times the total length 162. In the embodiment shown in the Figures, the ratio between the length 156 and the total length 162 is approximately 0.27 to approximately 0.28.

In the minimum 146, the cross-sectional area 144 of the rasp main body 12 has a value corresponding approximately to 0.5 to 0.8 times the cross-sectional area 144 in the region of the indentation 26. In the embodiment shown in the Figures, the ratio is approximately 0.62 to 0.7.

The rasp body part contact surface 32 and the side faces 40 and 42 adjoining it have rounded edges 164. Both the rasp main body 12 and the rasp body part 16 are each formed in one piece.

Figure 9:
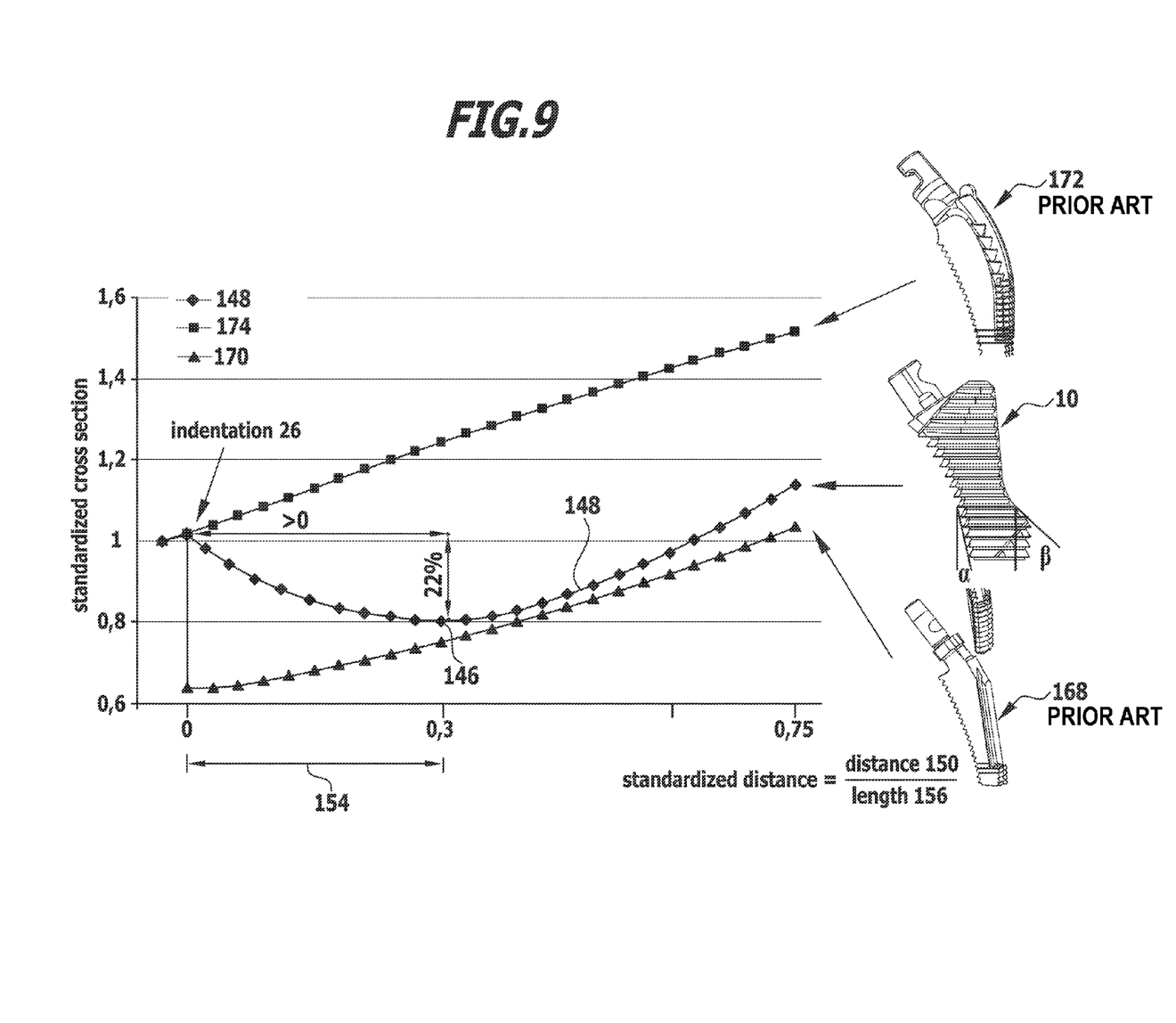
FIG. 9: shows a graphic representation of standardized cross sections of three prosthesis rasps.

Not only the function 148 of the standardized cross section in dependence upon the standardized distance 150 in relation to the length 156 is shown in FIG. 9. The function 170 is allocated to the rasp 168 shown at the bottom right in FIG. 9. The rasp 168 is shown in FIG. 9 in DE 10 2008 020 192 A1. The rasp 172 to which the function 174 is allocated is shown at the top right in FIG. 9. The rasp 172 is shown, for example, in FIG. 5 in DE 10 2008 020 192 A1.

The functions 148, 170 and 174 of the three rasps 10, 168 and 172 differ significantly. In the rasp 168, the standardized cross section decreases by more than 35% directly in the region of the indentation 26, which is recognizable as jump function. In contrast, in the rasp 10 described above the minimum 146 is very far from the indentation 26. In the rasp 172, the standardized cross-sectional area increases continuously starting from the indentation 26.

Figure 5:
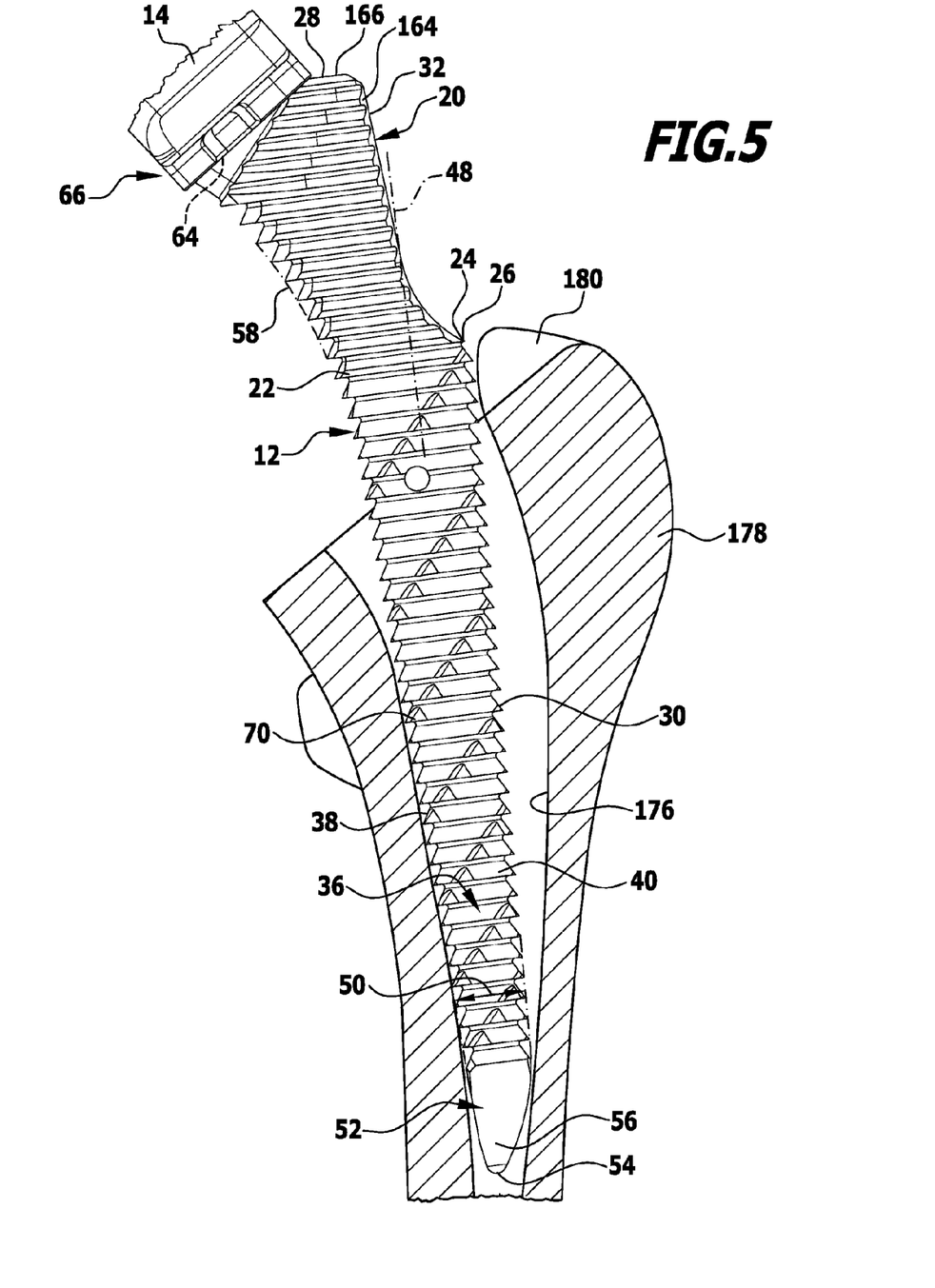
FIG. 5: shows an enlarged partial view of FIG. 1.

Owing to the special course of the function 148, it is possible to insert the stem 36 of the rasp body 18 into the medullary cavity 176 of a femur 178 after partial resection of the trochanter 180, without a remaining, protruding portion 182 of the trochanter 180, which points in the medial direction, being able to come into contact with the rasp main body 12. The special shape of the rasp body part contact surface 32 ensures, as is easy to recognize, in particular, in FIGS. 5 and 6, that the portion 182 of the trochanter 180 remains untouched irrespective of an insertion position of the rasp main body 12. Consequently, surrounding soft tissue is not traumatized either when inserting the rasp main body 12. When the stem 36 is inserted into the medullary cavity 176 the blunt tip 56 slides down the lateral cortex and thus forces the rasp main body 12 to rotate relative to an axis defined by the femur 178.

The insertion of the rasp main body 12 can take place between two extreme paths, which are defined by the respective most lateral points or regions of the rasp main body 12. In a conventional rasp, this point lies on the lateral side of the rasp main body, more specifically, at the point of intersection 188 of the path curves 184 and 186 drawn in broken lines in FIG. 6. The path curve 184 runs parallel to the longitudinal axis 48. Depending on the lateral range of such a rasp, in the case of the path curve 184 the trochanter 180 and the soft tissue are affected to a greater or lesser extent during the individual rasp operations. The other extreme path curve 186 runs as far medially as possible.

The shape of the path curve 186 is determined by the length of the rasp, the shape of its tip, the medial shape of the rasp and the shape of the bone. On this path curve 186, both the soft tissue and the trochanter region are affected to a significantly lesser extent. The rasping should therefore take place as far as possible on the path curve 186. In a clinical application, the actual course of the path curve will, however, move between the two described path curves 184 and 186.

When a rasp is being impacted, its lateral side moves on a large part of a rasp path along the cortex of the trochanter 180. Since this bone is very hard, the rasp 10, irrespective of whether rasp teeth 70 are laterally attached or not, is pressed in the medial direction. In order to avoid varus misalignment, the user must press against it appropriately. This, in turn, results in a rasp path that runs rather laterally. If the shoulder of the rasp is past the cortex, the remaining distance is too short to still straighten up a rasp that may already have tilted in the medial direction, before it reaches its final position. Ultimately, when using rasps known from the prior art, the user has the choice between an atraumatic path curve 186 running medially, where he risks a varus misalignment, and a traumatic lateral path curve 184 where he avoids a misalignment.

With the rasp 10 described above, these problems do essentially not occur. Owing to the particularly large rasp body part receptacle 20 and its special shape described above, both the trochanter 180 and surrounding soft tissue in this region are significantly spared, and a varus misalignment is avoided. Due to the provision of the rasp body part receptacle 20, the most lateral point of the rasp main body 12 is formed by the edge between rasp body part contact surface 32 and the side face 30 in the region of the indentation 26. The thus defined path curve 190 lies far below the optimum path curve 186 that is achievable with conventional rasps.

With the rasp 10, when it is being inserted into the medullary cavity 176, only the tip 56 lies against the cortex in the trochanter region, i.e., distally of the rasp body part receptacle 20. Once the tip 56 is past the cortex, there is no further contact between the rasp main body 12 and the cortex. The pressure on the rasp main body 12 therefore also diminishes. The remaining distance for straightening up the rasp main body 12 is considerably enlarged by the provision of the special rasp part receptacle 20, so that the rasp main body 12 is brought into the optimum position almost on its own by the stem 36. Therefore, differently from conventional rasps, the rasp main body 12 does not have to be pressed into its correct position by the user, but finds its way practically on its own.

Figure 7:
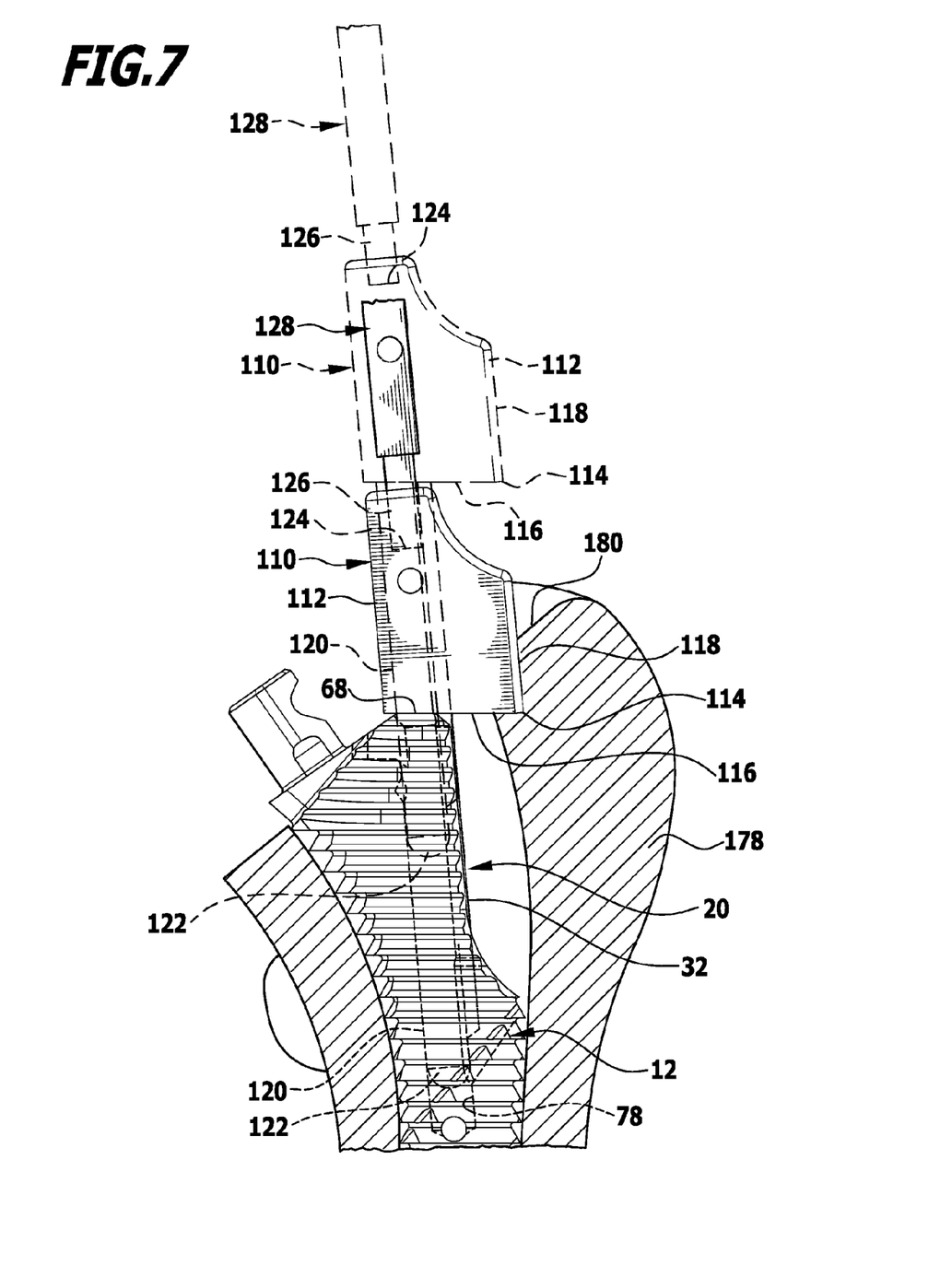
FIG. 7: shows a partially broken open side view of the rasp body inserted into the medullary cavity of the femur with the chisel part coupled to it.
Figure 8:
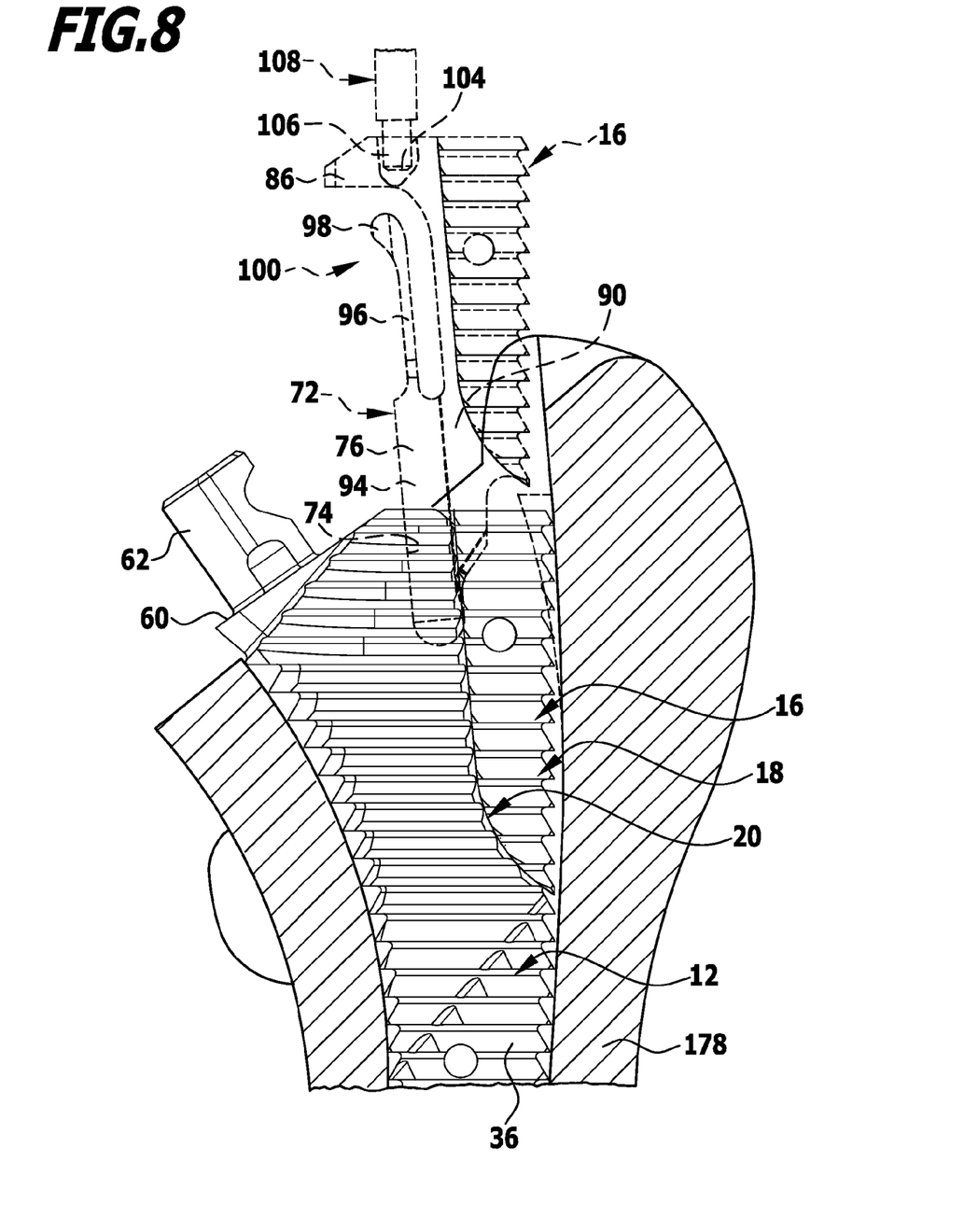
FIG. 8: shows a view similar to FIG. 7, but when the trochanter is being machined with the rasp body part.

Since the trochanter 180 is practically not machined after insertion of the rasp main body into the medullary cavity 176, the trochanter 180 is then prepared in advance and a portion thereof removed with the box chisel 110, as shown in FIG. 7. The then still remaining portion of the trochanter 180 is prepared by the rasp body part 16, more specifically, by it being connected in the manner described above to the rasp main body 12 and inserted from the proximal direction into the rasp body part receptacle 20. The still remaining protruding part 182 of the trochanter 180 is thereby simultaneously brought into the desired shape. Like the box chisel 110, the rasp body part 16 is thereby guided by the female connecting element 74.

The female connecting element 74 may also be useful as guide, alignment or orientation for various further instruments. Here, in particular, saw jigs, drilling templates and instruments for machining the bone in any shape are possible.

Depending on the patient's physiology, the modular prosthesis rasp 10 may also comprise further rasp body parts 16, which may differ in their shape and size from the rasp body part 16 shown in the Figures.

What is claimed is:

1. A modular prosthesis rasp, comprising:
    a rasp body comprising a rasp main body and at least one modular rasp body part connectable to the rasp main body,
    the rasp main body comprising a rasp body part receptacle for receiving the at least one rasp body part in a connected position in which the rasp main body and the at least one rasp body part are connected to each other,
    the rasp body defining an outer contour defined partly by the rasp main body and partly by the at least one rasp body part, and
    the rasp body part receptacle extending from an indentation, defining a distal end of the rasp body part receptacle, on a lateral side of the rasp main body to a proximal end of the rasp main body,
    wherein:
        a first tangential plane of the lateral side of the outer contour in a region of the indentation and a second tangential plane at a rasp body part contact surface, defined by the rasp body part receptacle and facing away from the rasp main body, in a region of the distal end of the rasp body part receptacle form an indentation angle which is less than 85°; and
        the rasp body part receptacle extends completely between side faces of the rasp main body which face away from each other.

2. The prosthesis rasp in accordance with claim 1, wherein the indentation angle has a value ranging from 20° to 70°.

3. The prosthesis rasp in accordance with claim 1, wherein the rasp body part contact surface defines a continuous surface.

4. The prosthesis rasp in accordance with claim 1, wherein the at least one rasp body part has a rasp main body contact surface, which in the connected position lies with surface-to-surface contact against the rasp body part contact surface.

5. The prosthesis rasp in accordance with claim 1, wherein the rasp body part contact surface has a planar first rasp body part contact surface region.

6. The prosthesis rasp in accordance with claim 5, wherein the first rasp body part contact surface region extends towards a proximal end of the rasp body part receptacle.

7. The prosthesis rasp in accordance with claim 5, wherein the first rasp body part contact surface region and a longitudinal axis of the rasp main body define an angle of inclination which has a value ranging from 0° to 25°.

8. The prosthesis rasp in accordance with claim 1, wherein the rasp body part contact surface has a second rasp body part contact surface region which is continuously curved.

9. The prosthesis rasp in accordance with claim 8, wherein the second rasp body part contact surface region has a constant radius of curvature.

10. The prosthesis rasp in accordance with claim 8, wherein the second rasp body part contact surface region extends as far as the distal end of the rasp body part receptacle.

11. The prosthesis rasp in accordance with claim 1, wherein a cross-sectional area of the rasp main body perpendicular to a longitudinal axis of the rasp main body, starting from the distal end of the rasp body part receptacle, decreases in a direction towards the proximal end of the rasp main body up to a minimum cross-sectional area and increases again from the minimum up to the proximal end.

12. The prosthesis rasp in accordance with claim 11, wherein a function of the cross-sectional area of the rasp main body perpendicular to the longitudinal axis, starting from the distal end of the rasp body part receptacle in the direction towards a proximal end of the rasp main body, forms, in dependence upon a distance of a cutting plane defining the cross-sectional area from the distal end of the rasp body part receptacle, a mathematically continuous function.

13. The prosthesis rasp in accordance with claim 11, wherein the minimum is at a distance from the distal end of the rasp body part receptacle, which corresponds to at least 0.1 times a length of the rasp body part receptacle parallel to the longitudinal axis.

14. The prosthesis rasp in accordance with claim 13, wherein the distance corresponds to at least 0.2 times the length of the rasp body part receptacle.

15. The prosthesis rasp in accordance with claim 1, wherein:
    a connecting device is provided for releasably connecting the rasp main body and the at least one rasp body part in the connected position, the connecting device comprises corresponding first and second connecting elements arranged or formed on the rasp main body and on the at least one rasp body part;

the first and second connecting elements are in engagement with each other in the connected position, the rasp main body comprises a female connecting element, and the at least one rasp body part comprises a corresponding male connecting element.

16. The prosthesis rasp in accordance with claim 15, wherein the female connecting element has a lateral guide slot which extends as far as the rasp body part contact surface.

17. The prosthesis rasp in accordance with claim 1, wherein a securing device is provided for securing a connection of the rasp main body and the at least one rasp body part in the connected position.

18. The prosthesis rasp in accordance with claim 1, wherein the rasp main body and the at least one rasp body part are movable relative to each other in the connected position.

19. The prosthesis rasp in accordance with claim 5, wherein the second tangential plane and the first rasp body part contact surface region form an obtuse included angle.

20. The prosthesis rasp in accordance with claim 19, wherein the obtuse included angle has a value ranging from 95° to 160°.

21. The prosthesis rasp in accordance with claim 5, wherein a length of the first rasp body part contact surface region parallel to a longitudinal axis of the rasp main body corresponds approximately to 0.4 times to 0.75 times a length of the rasp body part receptacle.

22. The prosthesis rasp in accordance with claim 1, wherein a length of the rasp body part receptacle parallel to a longitudinal axis of the rasp main body corresponds approximately to 0.15 times to 0.4 times a total length of the rasp main body.

23. The prosthesis rasp in accordance with claim 1, wherein a chisel part is provided, which is releasably connectable to the rasp main body.

24. A modular prosthesis rasp, comprising:
a rasp body comprising a rasp main body and at least one modular rasp body part connectable to the rasp main body, the rasp main body comprising a rasp body part receptacle for receiving the at least one rasp body part in a connected position in which the rasp main body and the at least one rasp body part are connected to each other, the rasp body defining an outer contour defined partly by the rasp main body and partly by the at least one rasp body part, and the rasp body part receptacle extending from an indentation, defining a distal end of the rasp body part receptacle, on a lateral side of the rasp main body to a proximal end of the rasp main body, wherein:
a cross-sectional area of the rasp main body perpendicular to a longitudinal axis of the rasp main body, starting from the distal end of the rasp body part receptacle, decreases in a direction towards the proximal end of the rasp main body up to a minimum cross-sectional area and increases again from the minimum up to the proximal end; and the rasp body part receptacle extends completely between side faces of the rasp main body which face away from each other.

25. A modular prosthesis rasp, comprising:
a rasp body comprising a rasp main body and at least one modular rasp body part connectable to the rasp main body, the rasp main body comprising a rasp body part receptacle for receiving the at least one rasp body part in a connected position in which the rasp main body and the at least one rasp body part are connected to each other, the rasp body defining an outer contour defined partly by the rasp main body and partly by the at least one rasp body part, and the rasp body part receptacle extending from an indentation, defining a distal end of the rasp body part receptacle, on a lateral side of the rasp main body to a proximal end of the rasp main body, wherein:
a connecting device is provided for releasably connecting the rasp main body and the at least one rasp body part in the connected position, the connecting device comprises corresponding first and second connecting elements, arranged or formed on the rasp main body and on the at least one rasp body part, the first and second connecting elements are in engagement with each other in the connected position, the rasp main body comprises a female connecting element, and the at least one rasp body part comprises a corresponding male connecting element; and a cross-sectional area of the rasp main body perpendicular to a longitudinal axis of the rasp main body, starting from the distal end of the rasp body part receptacle, decreases in a direction towards the proximal end of the rasp main body up to a minimum cross-sectional area and increases again from the minimum up to the proximal end; and the rasp body part receptacle extends completely between side faces of the rasp main body which face away from each other.

* * * * *